United States Patent [19]

Thomas

[11] Patent Number: 4,883,473
[45] Date of Patent: Nov. 28, 1989

[54] SINGLE USE INJECTION DEVICE

[75] Inventor: Ronny D. Thomas, Bellevue, Wash.

[73] Assignee: Path, Seattle, Wash.

[21] Appl. No.: 199,612

[22] Filed: May 27, 1988

Related U.S. Application Data

[63] Continuation-in-part of Ser. No. 44,054, Apr. 29, 1987.

[51] Int. Cl.[4] .......................... A61M 5/18; A61M 5/32
[52] U.S. Cl. ..................... 604/217; 604/132; 604/204; 222/95; 222/107; 222/215
[58] Field of Search ............... 604/217, 204, 132, 198, 604/411, 413; 222/92, 95, 107, 206, 215

[56] References Cited

U.S. PATENT DOCUMENTS

| | | | |
|---|---|---|---|
| 1,948,306 | 2/1934 | Meurer | 604/204 X |
| 2,667,872 | 2/1954 | Smith | 604/204 X |
| 3,128,920 | 4/1964 | Volckening et al. | 222/215 |
| 3,252,625 | 5/1966 | Cattaneo | 222/215 X |
| 3,335,914 | 8/1966 | Stanzdins et al. | 222/107 |
| 3,496,937 | 2/1970 | Balsom | 604/132 |
| 3,512,524 | 5/1970 | Drewe | 604/204 X |
| 3,552,604 | 1/1971 | Gordon | 222/215 |
| 4,261,482 | 4/1981 | Yamada et al. | 222/215 |
| 4,618,224 | 4/1977 | McAleer et al. | 604/204 X |
| 4,758,230 | 7/1988 | Rycroft | 222/604 |

Primary Examiner—Carl D. Price
Attorney, Agent, or Firm—Finnegan, Henderson, Farabow, Garrett & Dunner

[57] ABSTRACT

A single use, single dose injection administering device including a drug or vaccine containing body and a needle wherein the sidewalls have memory causing at least one sidewall to collapse into the other during the administration of the vaccine.

1 Claim, 3 Drawing Sheets

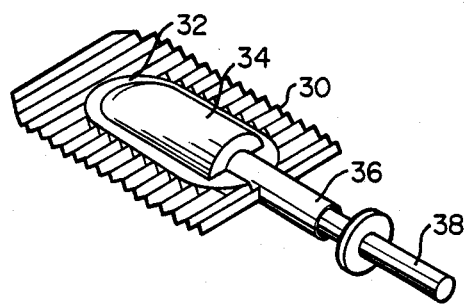
FIG. 5
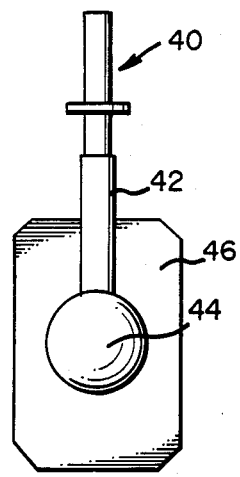 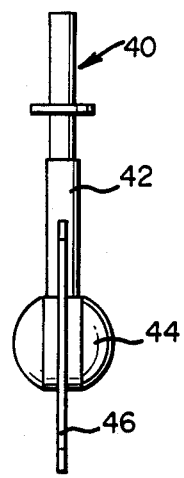 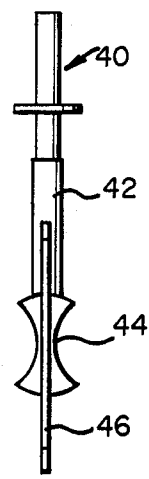
FIG. 6    FIG. 7    FIG. 8
FIG. 9

SINGLE USE INJECTION DEVICE

FEDERALLY-SPONSORED RESEARCH AND DEVELOPMENT

The U.S. Government has contributed support to this invention under Federal Grant No. DPE-5968-A-00-7035-00 awarded by the Agency for International Development. The U.S. Government has certain rights in the invention.

This is a continuation-in-part application of Ser. No. 044,054 filed Apr. 29, 1987.

TECHNICAL FIELD

This invention relates to single dose, single use injection device and, more particularly, to an injection device which is easily used in the field by non-professional but trained personnel and the device is rendered incapable of reuse following the intended use.

BACKGROUND ART

Conventional administration of vaccine or other injectable drugs via a reusable syringe is a perfectly adequate and an economic approach where the administration is done by professional staff and in facilities where the circulation of the syringe can be managed and controlled. The syringe can then be sterilized for reuse, refilled and administered by trained, skilled professional personnel.

There are, however, situations where injections are given to large numbers of individuals over a short period of time and where it is virtually impossible to sterilize equipment and further, the administration of the drug or vaccine will be done by non-professional but trained personnel. Because of cost, these situations typically preclude use of a standard disposable syringe. It is known that for these circumstances, a single dose prefilled vaccine delivery system has been developed wherein the single dosage syringe has a squeezable body portion permitting the rapid administration of the dose.

Prior art devices which deal with the area of disposable syringes include U.S. Pat. No. 2,618,263 granted to Lakso Nov. 18, 1952 discloses a single use syringe wherein the needle and the medicant containing portion are encapsulated in a rigid envelope, the top portion being broken off to expose the injection needle and the bottom portion includes a window-like portion such that the bladder may be compressed and the medicant expressed.

U.S. Pat. No. 4,013,073 granted to Cunningham on Mar. 22, 1977 discloses a dispensing device wherein the medicant containing syringe portion includes an internally facing interacting interlock system that when the walls of the bladder portion are squeezed the inner surfaces interlock preventing reuse.

U.S. Pat. No. 4,022,206 granted to Hilleman et al on May 10, 1977 discloses a vaccine delivery system including single dosage syringes having a squeezable body portion and a separate package containing water to reconstitute lyophilized vaccine.

U.S. Pat. No. 4,391,273 granted to Chiquiararias on July 5, 1983 discloses a non-reusable disposable syringe wherein the use of the piston effectively destroys the syringe.

U.S. Pat. No. 4,548,601 granted to Lary on Oct. 22, 1985 discloses a pharmaceutical and hypodermic needle combination including a semi-rigid outer container surrounding a substantially nonresilient inner container which contains the premeasured dose of the pharmaceutical. When administered the interior envelope collapses and remains in the collapsed condition.

The reuse of the prior art devices which are not self-destructing presents a problem in that the device is no longer sterile and, therefore, the risk of infection is great. Further, often times the reuse typically occurs in settings outside the formal health care system. The rapid spread of acquired immune deficiency syndrome among intravenous drug users has occurred in part due to this reuse.

Those prior art devices which are not capable of reuse are expensive to manufacture and/or are bulky and thus inconvenient to ship and store.

In addition, most of the devices fail to provide the capability for performing aspiration to determine proper placement of the needle. In performing an injection, medical practitioners are trained to "aspirate" before injecting in order to confirm whether the needle is or is not in a blood vessel. Aspiration is accomplished by drawing a negative or suction pressure and visually examining for blood that is transferred into the medicant solution through the needle. In the administration of an intravenous injection the presence of blood indicates proper placement. In the administration of an intramuscular injection, the presence of blood indicates improper placement. Aspiration is not possible at any time in the use of many of the prefilled devices as the contents of the receptacle are under a positive pressure to express the medicant.

The functional requirements for a product that allows aspiration as well as a means for providing a positive internal pressure to prevent subsequent refilling have conflicted in prior art devices.

DISCLOSURE OF THE INVENTION

It is an object of the present invention to provide a single dose, single use injection device which cannot be reused.

Another object of the present invention is to provide a single use, single dose injection device wherein the container is self-collapsing when emptied but has sufficient integrity to permit aspiration during the early stages of administration.

Still another object of the present invention is to provide a single use, single dose injection device wherein the act of administering the contents renders the device non-reusable.

Yet another object of the present invention is to provide a single use injection device wherein the mere fact of usage renders the device incapable of reuse but also a device which is capable of use with a lyophilized drug or vaccine requiring reconstitution with a diluent.

Yet a further object of the present invention is to utilize a fabrication process for the inventive device which incorporates one or more steps which prestress or deform a portion of the container such that it remains collapsed if empty.

BRIEF DESCRIPTION OF THE DRAWINGS

FIG. 5 depicts the inventive container as would be formed in a blister pack i.e. two thermoformed sheets joined together to form a container shaped to accomplish the pressure profile.

FIG. 6 is a front elevational view of another embodiment of the present invention.

FIG. 7 is a side elevational view of the embodiment of FIG. 6 depicting the syringe in its ready to use or filled condition.

FIG. 8 is a side elevation of the syringe of FIG. 6 when the syringe is emptied and in a non-reusable condition.

FIG. 9 is a side elevation of yet another embodiment.

BEST MODE FOR CARRYING OUT THE INVENTION

Figure 1:
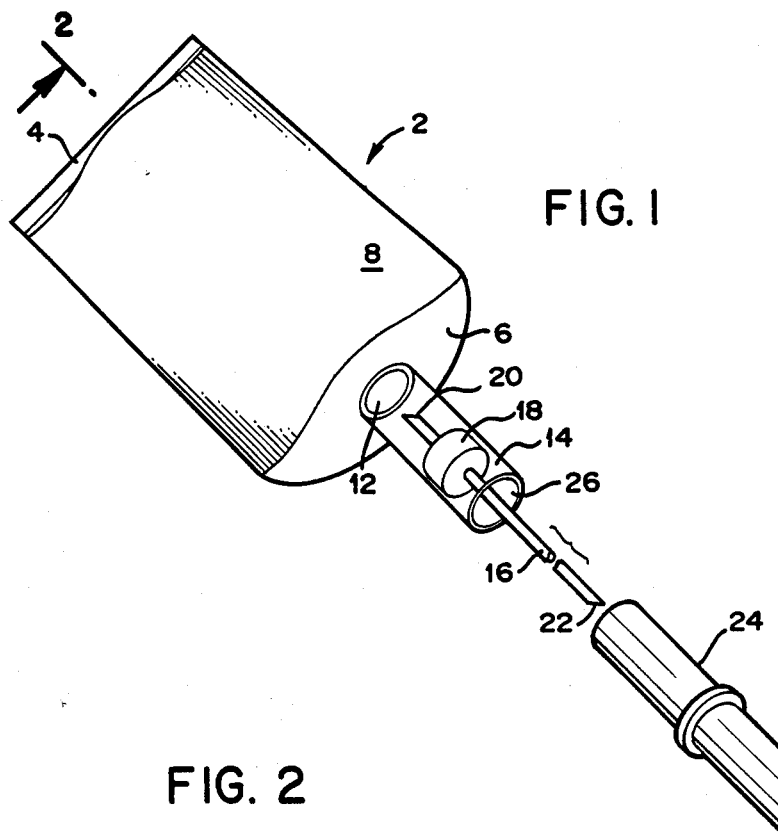
FIG. 1 is a pictorial representation of the inventive device when filled for shipping and storing. The cap is shown exploded for clarity.

As seen in FIG. 1, the single use/single dosage immunization device includes a main body portion generally designated as 2 having a flat generally linear bottom seal 4 and a bridging or interlinking upper member 6 such that it retains the convex sides 8, 10 in a separated condition, supports the containment membrane 12 and provides a foundation for outwardly extending nozzle member 14.

A needle 16 passes through a needle hub 18 which is frictionally held within the nozzle 14. It is to be noted that needle 16 has a sharpened inner end portion 20 for penetrating membrane 12 and a sharpened outer end portion 22 for use in administering the drug or vaccine.

A needle protector 24 having a diameter such that it can fit within nozzle member 14 is, for storage and shipment, lodged with its open end fitting within the open end of nozzle 14 and held in position by a combination of friction and an inwardly projecting annular ridge 26 which abuts hub 18. Needle protector 24 includes an outwardly projecting flange 25 to control the movement when preparing to administer the solution by forcing needle end 22 through membrane 12.

Figure 2:
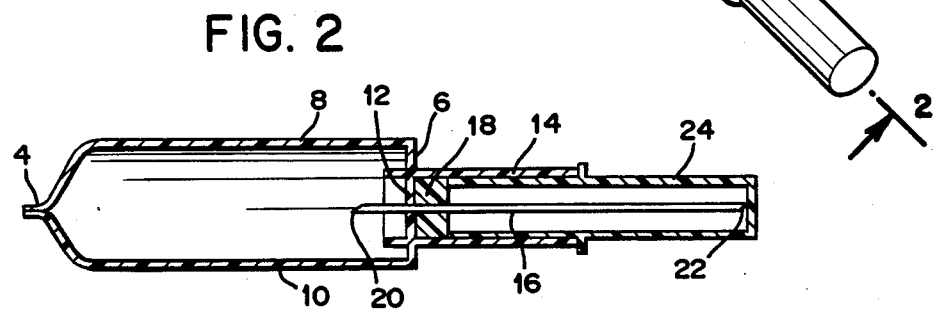
FIG. 2 is a sectional view along lines 2—2 of FIG. 1 with the cap in place, the needle in position for application and, in phantom, the cap in the position it would assume when inserting the needle into the container.

Referring now to FIG. 2, the device is shown in a configuration after the needle protector 24 has been used as a tool to force the needle hub 18 out of its friction-held position within 14 rearwardly such that the sharp point 20 of needle 16 has penetrated membrane 12. It is to be noted that the needle protector 24 is of such a size that it surrounds the needle 16, abuts against the outer surface of plug 18 and yet does not contact point 22. Following the piercing of the diaphragm 12 the needle protector 24 is removed and can be retained for use as a protective cover over the needle once the injection has been administered.

Figure 3:
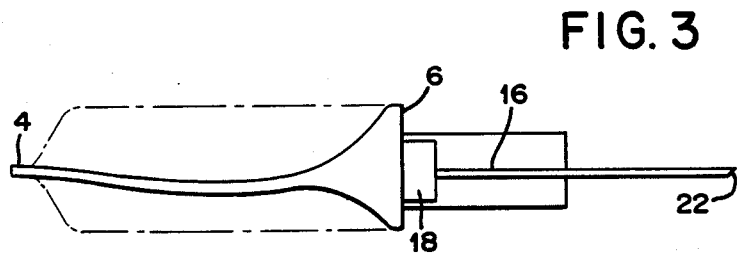
FIG. 3 is a side view of the present invention with the container body collapsed.

As seen in FIG. 3, the sides of the container are squeezed and collapsed during the administration of the drug or vaccine and once the drug or vaccine has been expelled, the memory of the sidewalls becomes controlling and, as one convex side folds into the opposite side, results in a container which cannot be easily reused because the final shape of the collapsed container cannot be overcome with the application of external pressure to draw another dose. The device is for illustrative purposes only and the identical results could be achieved by incorporating stress during fabrication or by pleats or cuts which cause a predisposition to the collapsed condition.

Figure 4:
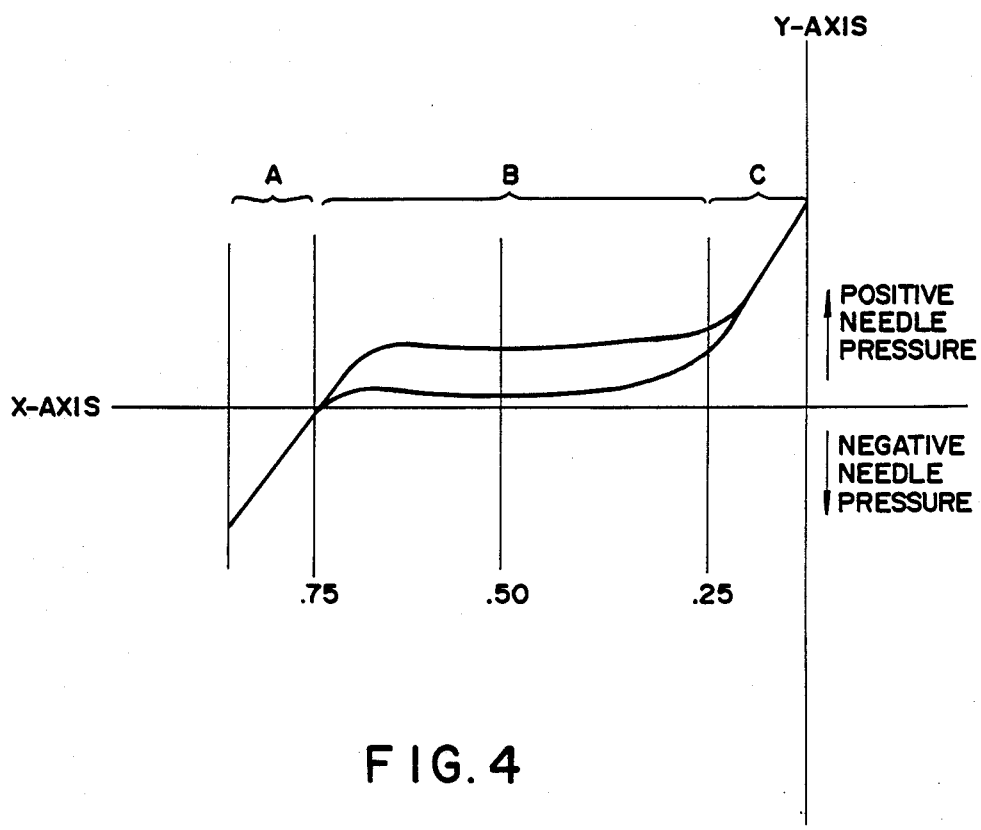
FIG. 4 is a graph depicting the interrelationship of the volume within the device and the needle pressure.

Reference is now had to FIG. 4 which is a graphical presentation of the volume of the fluid within the device plotted against the needle pressure as the drug or vaccine is administered. As can be seen, when the device is full there is in essence a negative needle pressure. At the left hand side of the graph in the zone denoted by A the person applying the fluid can aspirate to make sure that the needle is properly placed. The shape and structure of the container is such that the aspiration does not collapse the container. The infusion zone, noted as B, occurs during the administration of the injection and pressure is applied to the sidewalls of the container. When the container is approximately three-fourths empty, the memory of the sidewalls is caused to react and as the last of the drug or vaccine is infused, the sidewalls collapses into the other rendering the device not capable or reuse.

As seen in FIG. 5, an application of the present invention to a mass produced vacuum formed sheet device can be seen wherein the sheet material is generally designated as 30 and in finished form is somewhat serrated but includes a sealed closing zone 32 surrounding a vaccine containing pouch 34 the sides of which will be prestressed or given memory as hereinabove described. A nozzle 36 containing a needle as described hereinabove and a protector cap 38 are likewise shown. This method of fabrication lends itself to mass produced large volume low cost items.

Reference is now had to FIGS. 6, 7 and 8 wherein yet another embodiment is shown. In this embodiment, the needle assembly generally designated as 40 includes the needle and the protective dust cap which is mated with the neck 42 which is in fluid communication with the main storage section 44. The main storage section or body 44 is, in fact, vacuum molded from a pair of contiguous sheets 46 which are heat sealed around the edges to form the storage section 44, i.e. the main body portion 44 is left unsealed and drawn into a vacuum mold.

Reference to FIG. 7 discloses a side elevation of the syringe and in this embodiment the main reservoir 44 is spherical in configuration when the syringe is ready to use.

Yet another alternate embodiment is depicted in FIG. 9 wherein the main body portion is in the form of a short cylinder having outwardly curved end panels.

As explained hereinabove, with respect to the other embodiments, the primary purpose of the present invention is to provide a syringe which is of single dosage, convenience and yet which is rendered difficult if not impossible to reuse. As seen in FIG. 8, the administrator of the material in the syringe aspirates to determine the appropriate placement of the needle and then squeezes both sides of the sphere 44 causing it to collapse, as seen in this figure, rendering the device extremely difficult or impossible to reuse.

Thus as can be seen, the present invention contemplates an injection administering device where either liquid or lyophilized drugs or vaccine can be preloaded by applying adequate external pressure to overcome the memory of the sidewalls. In the case of the lyophilized drug or vaccine, the drug or vaccine can be reconstituted by administering sterile water or by rupturing a seal between two adjacent compartments within one container, one compartment containing water and the other lyophilized material.

Once the drug or vaccine has been applied, the disposable device is completely collapsed, strongly discouraging reuse.

I claim:

1. A single-use disposable syringe for providing a medicament for injection into a patient, the syringe comprising:

a needle portion for injecting the medicament into the patient;

a main body portion for storing the medicament and for expelling the medicament into the needle portion, the main body portion including:
- a compressible outwardly curved first end panel,
- a compressible outwardly curved second end panel, and
- a cylindrical bridging member, coupled to the first and second end panels, for separating the first and second end panels, to enable each of the end panels to become concave in response to complete compression of both of the end panels together; and a neck portion coupled to the needle portion and to the main body portion for directing the medicament from the main body portion to the needle portion;

wherein the main body portion substantially collapses in response to complete compression of both of the end panels together to prevent the main body portion from being reformed and to expel the medicament out of the main body portion;

wherein in response to partial compression of both of the end panels together, the main body portion partially collapses to expel some of the medicament out of the main body portion; and wherein the end panels, after partial compression of the end panels together and partial collapse of the main body portion, expand to reform the outwardly curved end panels of the main body portion, thereby drawing fluid into the main body portion and aspirating the needle portion.

* * * * *